US012778483B2

(12) United States Patent
Juurakko et al.

(10) Patent No.: US 12,778,483 B2
(45) Date of Patent: Nov. 3, 2026

(54) SYSTEM AND APPARATUS FOR MONITORING AND ASSESING CARDIAC ARRHYTHMIAS

(71) Applicant: GE Precision Healthcare LLC, Wauwatosa, WI (US)

(72) Inventors: Juliaana Juurakko, Uusimaa (FI); Heikki Paavo Aukusti Väänänen, Uusimaa (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 901 days.

(21) Appl. No.: 17/747,535

(22) Filed: May 18, 2022

(65) Prior Publication Data

US 2023/0371878 A1 Nov. 23, 2023

(51) Int. Cl.
*A61B 5/364* (2021.01)
*A61B 5/00* (2006.01)
*A61B 5/024* (2006.01)
*A61B 5/308* (2021.01)

(52) U.S. Cl.
CPC ............ *A61B 5/364* (2021.01); *A61B 5/0006* (2013.01); *A61B 5/02416* (2013.01); *A61B 5/308* (2021.01); *A61B 5/746* (2013.01)

(58) Field of Classification Search
CPC ..... A61B 5/364; A61B 5/02416; A61B 5/308; A61B 5/746; A61B 5/361; A61B 5/7264
See application file for complete search history.

(56) References Cited

U.S. PATENT DOCUMENTS

| | | | | |
|---|---|---|---|---|
| 7,846,106 | B2 | 12/2010 | Andrews | |
| 9,572,538 | B2 | 2/2017 | Sitzman | |
| 9,629,566 | B2 | 4/2017 | Gilham | |
| 10,699,811 | B2 | 6/2020 | Gilham | |
| 10,729,350 | B2 | 8/2020 | Kaski | |
| 11,139,077 | B2 | 10/2021 | Gilham | |
| 2019/0282118 | A1* | 9/2019 | Kaski .................. | A61B 5/7282 |
| 2020/0294660 | A1 | 9/2020 | Gilham | |
| 2020/0303067 | A1 | 9/2020 | Gilham | |
| 2021/0369209 | A1* | 12/2021 | Braun .................. | A61B 5/0245 |
| 2022/0313098 | A1* | 10/2022 | LeBoeuf .............. | A61B 5/7221 |

OTHER PUBLICATIONS

Deshmane, Anagha, "False arrhythmia alarm suppression using ECG, ABP, and photoplethysmogram," 2009, Max Planck Institute for Biological Cybernetics, 94 pages.

* cited by examiner

*Primary Examiner* — Niketa Patel
*Assistant Examiner* — Sebastian X Lukjan

(57) ABSTRACT

A system for monitoring cardiac arrhythmias including an ECG monitor configured to obtain ECG data, the ECG data being obtained by measuring cardiac potentials during cardiac cycles; a blood flow monitor configured to obtain secondary data, the secondary data being obtained by measuring a physiological parameter indicative of blood flow; a memory storing instructions; and one or more processors configured to execute the instructions to: detect a presence of an arrhythmia based on the ECG data; classify a pulse segment of secondary data obtained during the arrhythmia based on pulse morphology; assign a segment value to the pulse segment based on the classification; calculate a shortage value based on a previous shortage value and the segment value; and generate an arrhythmia severity indicator based on the shortage value.

20 Claims, 12 Drawing Sheets

SYSTEM AND APPARATUS FOR MONITORING AND ASSESING CARDIAC ARRHYTHMIAS

BACKGROUND

This disclosure generally relates to the field of patient monitoring and, more particularly to a system and apparatus for monitoring and assessing cardiac arrhythmias.

Currently available patient monitoring systems including electrocardiographs (ECG) typically have algorithms for detecting and identifying various arrhythmias. However, these machines are unable to judge a severity of the arrythmia. For a sever arrythmia, immediate medical attention may be necessary, while for a mild arrythmia medical attention may not be necessary. Additionally, the ECG signal can be corrupted by noise and other factors which can trigger a false alarm.

BRIEF DESCRIPTION

This Brief Description is provided to introduce a selection of concepts that are further described below in the Detailed Description. This Summary is not intended to identify key or essential features of the claimed subject matter, nor is it intended to be used as an aid in limiting the scope of the claimed subject matter.

According to an aspect of the disclosure, a system for monitoring cardiac arrhythmias may include: an ECG monitor configured to obtain ECG data, the ECG data being obtained by measuring cardiac potentials during cardiac cycles; a blood flow monitor configured to obtain secondary data, the secondary data being obtained by measuring a physiological parameter indicative of blood flow; a memory storing instructions; and one or more processors configured to execute the instructions to: detect a presence of an arrhythmia based on the ECG data; classify a pulse segment of secondary data obtained during the arrhythmia based on pulse morphology; assign a segment value to the pulse segment based on the classification; calculate a shortage value based on a previous shortage value and the segment value; and generate an arrhythmia severity indicator based on the shortage value.

The ECG monitor may include one of a 5 lead, an 8 lead, and a 12 lead ECG monitoring system.

The blood flow monitor may include a blood pressure monitor configured to provide a continuous blood pressure measurement.

The blood flow monitor may include a pulse oximeter configured to provide a photoplethysmography measurement.

The one or more processors may be further configured to execute the instructions to trigger or escalate an alarm indicating a cardiac arrhythmia in response to the shortage value exceeding a predefined threshold.

The pulse segment classifications may include a normal pulse, an altered pulse, and a missed pulse.

The one or more processors may be further configured to execute the instructions to assign a value to each pulse segment by: assigning a first segment value based on a pulse segment being classified as having an altered pulse; assigning a second segment value based on a pulse segment being classified as having a missed pulse; and assigning a third segment value based on a pulse segment being classified as having a normal pulse. The first segment value, the second segment value, and the third segment value may each have different values.

The one or more processors may be further configured to execute the instructions to calculate the first segment value by: calculating an integral of the oxygen saturation data over the pulse segment; dividing the integral by a length of the pulse segment to obtain a relative integral of the pulse; subtracting the relative integral of the pulse from a relative integral of the reference pulse to obtain a pulse difference; and dividing the pulse difference by the reference integral of the reference pulse.

The third segment value may be a preset value and the second segment value may be an additive inverse of the third segment value.

The one or more processors may be further configured to execute the instructions to: detect a heart beat in the ECG data during the pulse segment; detect a pulse in the oxygen saturation data during the pulse segment; and based on detecting the heart beat in the ECG data and not detecting a pulse in the oxygen saturation data, determine that the pulse segment is a missed pulse.

The one or more processors may be further configured to execute the instructions to classify the normal pulse and the altered pulse by comparing the pulse segment to a reference pulse.

The one or more processors may be further configured to execute the instructions to obtained the reference pulse based on previously recorded secondary data during beats classified as normal based on the ECG data.

The one or more processors may be further configured to execute the instructions to obtain reference pulse based on one or more of a median pulse or a mean pulse of the previously recorded secondary data.

The arrythmia severity indicator may include a shortage index based on the shortage value and at least one previous shortage value.

The one or more processors may be further configured to execute the instructions to calculate the segment value by multiplying a slope of the pulse segment by a length of the pulse segment.

The one or more processors may be further configured to execute the instructions to set the pulse segment based on a segment of the ECG data corresponding to a heartbeat.

According to another aspect of the disclosure, a system for monitoring cardiac arrhythmias may include: an ECG monitor configured to obtain ECG data, the ECG data being obtained by measuring cardiac potentials during cardiac cycles; a blood flow monitor configured to obtain secondary data, the secondary data being obtained by measuring a physiological parameter indicative of blood flow; a memory storing instructions; and one or more processors configured to execute the instructions to: detect a presence of an arrhythmia based on the ECG data; classify a pulse segment of secondary data obtained during the arrhythmia based on pulse morphology; assign a slope to the pulse segment based on the classification; multiply the slope of the pulse segment by a length of the pulse segment to obtain a segment value; calculate a shortage value by adding a previous shortage value and the segment value; compare shortage value to a predefined threshold; and trigger an alarm based on the shortage value exceeding a predefined threshold.

The pulse segment classifications may include a normal pulse, an altered pulse, and a missed pulse. The one or more processors may be further configured to execute the instructions to assign a value to each pulse segment by: assigning a first segment value based on a pulse segment being classified as having an altered pulse; assigning a second segment value based on a pulse segment being classified as having a missed pulse; and assigning a third segment value based on a pulse segment being classified as having a normal pulse. The first segment value, the second segment value, and the third segment value may each have different values.

The one or more processors may be further configured to execute the instructions to calculate the first segment value by: calculating an integral of the oxygen saturation data over the pulse segment; dividing the integral by a length of the pulse segment to obtain a relative integral of the pulse; subtracting the relative integral of the pulse from a relative integral of the reference pulse to obtain a pulse difference; and dividing the pulse difference by the reference integral of the reference pulse.

The third segment value may be a preset value and the second segment value may be an additive inverse of the third segment value.

According to another aspect of the disclosure, a method for monitoring cardiac arrhythmias may include: detecting a presence of an arrhythmia based on ECG data; classifying a pulse segment of secondary data obtained during the arrhythmia based on pulse morphology, the secondary data indicating blood flow; assigning a segment value to the pulse segment based on the classification; calculating a shortage value based on a previous shortage value and the segment value; and generating an arrhythmia severity indicator based on the shortage value.

The pulse segment classifications may include a normal pulse, an altered pulse, and a missed pulse. Assigning a value to each pulse segment may include: assigning a first segment value based on a pulse segment being classified as having an altered pulse; assigning a second segment value based on a pulse segment being classified as having a missed pulse; and assigning a third segment value based on a pulse segment being classified as having a normal pulse, wherein the first segment value, the second segment value, and the third segment value each have different values.

Calculating the first segment value may include calculating an integral of the oxygen saturation data over the pulse segment; dividing the integral by a length of the pulse segment to obtain a relative integral of the pulse; subtracting the relative integral of the pulse from a relative integral of the reference pulse to obtain a pulse difference; and dividing the pulse difference by the reference integral of the reference pulse. The third segment value may be a preset value and the second segment value is an additive inverse of the third segment value.

BRIEF DESCRIPTION OF THE DRAWINGS

The present disclosure is described with reference to the following Figures.

DETAILED DESCRIPTION

The inventor has recognized that given the prevalence of arrhythmias, measurement of the severity of the arrhythmia can be important to maximize the effectiveness of patient monitoring and to facilitate detection and treatment of the most severe arrhythmias. The severity of an arrhythmia depends on its effect on the blood circulation in the patient's body. For example, the most critical arrythmia incidence may cause circulation to temporarily stop, while less critical arrhythmias may maintain consistent circulation at the appropriate level for the patient. Thus, the inventor recognized that the severity of an arrhythmia, and thus its criticality to the patient's current health condition, can be measured according to its effect on hemodynamics.

Moreover, the inventor realized that such information can provide valuable information for real-time patient monitoring, and that such information can be immediately reported at part of the patient physiological monitoring and incorporated into alarming algorithms so that clinicians can be informed of the severity of an arrhythmia event and alerted to the most severe events. As disclosed herein, pulse waveform data provided by an arterial blood flow monitor is used to determine hemodynamic impact of an arrythmia. The hemodynamic impact is evaluated using a perfusion shortage algorithm which classified the pulses in the pulse waveform data and assigns a value to each pulse. The perfusion shortage algorithm determines a current hemodynamic impact based on a cumulative function which inputs the pulse values.

Figure 1:
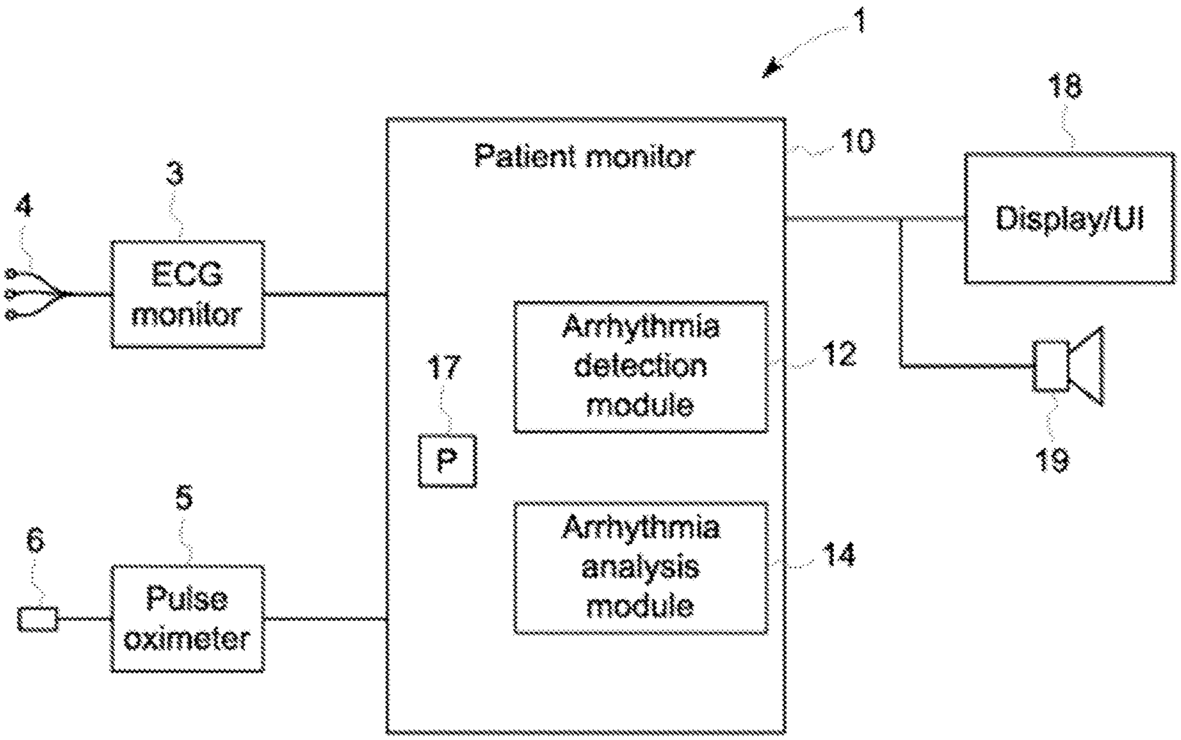
FIG. 1 schematically depicts an exemplary patient monitoring system for monitoring cardiac arrhythmias.

FIG. 1 schematically depicts an exemplary patient monitoring system 1 for monitoring cardiac arrhythmias. In the example shown in FIG. 1, the patient monitoring system 1 includes a patient monitor 10 receiving information from an ECG monitor 3 and an arterial blood flow monitor 5, which in the depicted embodiment is a pulse oximeter. The cardiac potentials generated by the ECG monitor 3 and the pulse waveform generated by the arterial blood flow monitor 5 are provided to a patient monitor 10 that gathers, correlates, and analyzes the cardiac and pulse information. In various embodiments, the ECG monitor 3 and/or the arterial blood flow monitor 5 may be incorporated in a single, multi-parameter patient monitor 10 that receives the cardiac and pulse waveform information collected from the patient and generates the cardiac potentials and pulse waveform data accordingly. In other embodiments, the patient monitor 10 may be a separate device (such as a hub or central patient monitor device) that receives information from various separate monitors receiving and analyzing patient physiological data, including the ECG monitor 3 and the arterial blood flow monitor 5. In still other embodiments, the ECG monitor 3 and the arterial blood flow monitor 5 may communicate with one another to provide comprehensive patient monitoring, and each device may then communicate the patient monitoring information to the patient's medical record, such as stored on the network of the healthcare facility and/or on the cloud. For example, the ECG monitor 3 may incorporate the arrhythmia detection module 12 to detect an arrhythmia, and may communicate information regarding arrhythmia detection and the timing of the QRS wave to the arterial blood flow monitor 5. The arterial blood flow monitor 5 may similarly incorporate the arrhythmia analysis module 14 to determine an arrhythmia severity indicator as described herein.

The ECG monitor is recording and measuring cardiac potentials from a patient via two or more electrodes 4 connected to the patient. Various forms of ECG electrodes 4 and/or electrode systems are well known and available in the art, any of which may be utilized to record cardiac potentials from the patient. Additionally, any number of two or more ECG electrodes 4 may be utilized. In one embodiment, 10 ECG electrodes 4 are connected to the patient, and the ECG monitor 3 is configured to generate a standard 12 lead ECG. In other embodiments, fewer or more electrodes may be utilized and cardiac potentials may be generated for a smaller or greater number of leads by the ECG monitor 3.

The arterial blood flow monitor 5 measures arterial blood flow for the patient and generates pulse waveform data representing blood flow changes during the cardiac cycles. In the depicted embodiment, the arterial blood flow monitor 5 is a pulse oximeter. In other embodiments, the arterial blood flow monitor 5 may be an invasive or noninvasive continuous blood pressure monitor, which are well known in the art. The pulse oximeter 5 is connected to a pulse oximetry probe 6 that attaches to a patient, such as the patient's finger or ear, to measure the blood flow at that location during the cardiac cycles. Such probe 6 is well known in the art, often utilizing red and infrared light to measure changes in blood flow throughout the cardiac cycle.

The pulse oximeter and/or continuous blood pressure monitor then generate pulse waveform data representative of arterial blood flow during the cardiac cycles monitored by the ECG monitor. The cardiac potentials and the pulse waveform data can be synchronized according to the time of recordal, and thus correlations can be drawn between the cardiac cycles as measured by the cardiac potentials and the resulting measured blood flow at the measurement location of the arterial blood flow monitor 5.

In the depicted embodiment, the patient monitor 10 includes an arrhythmia detection module 12 and an arrhythmia analysis module 14, both being sets of software instructions configured to perform certain functions. The arrhythmia detection module 12 may process the cardiac potentials from the ECG monitor 3 to detect that presence or absence of an arrhythmia, and to generate an arrhythmia indicator upon detecting the presence of the arrhythmia. Thus, the arrhythmia detection module 12 may inform the arrhythmia analysis module 14 when an arrhythmia is occurring, and such information is used to trigger analysis of the severity of the arrhythmia by the arrhythmia analysis module 14.

Various such arrhythmia detection modules 12 are available and known in the art for analyzing ECG potentials and detecting arrhythmias based thereon. For example, the Marquette 12SL® ECG analysis program by General Electric Company of Schenectady, New York, is an exemplary computerized analysis program providing measurements of heartrate, axis, intervals, and durations of heartrate waveforms, as well as interpretive statements offering automated ECG data analysis, such as arrhythmia detection, pace detection, waveform feature identification, etc. Other systems and software products are well known and available in the art providing arrhythmia detection.

Figure 2:
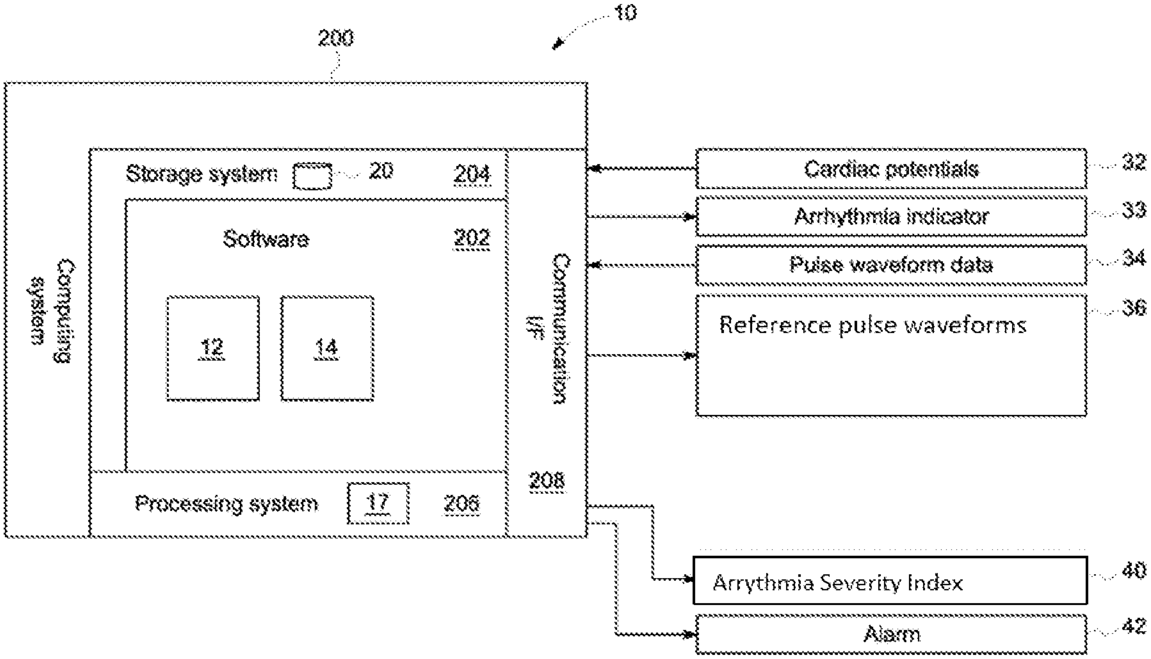
FIG. 2 is a block diagram illustrating an exemplary computing system of a patient monitoring system monitoring cardiac arrhythmias of a patient.

With further reference to FIG. 2, the arrhythmia analysis module 14 may be a set of software instructions configured to estimate a hemodynamic impact of an arrhythmia based on pulse waveform data 34. The arrhythmia analysis module 14 may obtain a reference pulse waveform from a time in which no arrhythmia is detected in ECG data. When an arrhythmia is detected in ECG data, each pulse segment of the pulse waveform data 34 may be classified based on pulse morphology. A value may then by assigned to the pulse segment based on the classification and the pulse morphology. The arrhythmia analysis module 14 may then generate an arrythmia severity index 40 based on the values of the pulse segments. As such, arrythmia severity index 40 may to indicate a hemodynamic impact of an arrythmia, thus indicating the severity of the arrythmia. As such, the arrythmia severity index 40 may be an arrythmia severity indicator.

In various embodiments, the arrhythmia severity index 40 may be updated for each pulse segment based on the pulse waveform data 34. In such an embodiment, the arrhythmia severity index 40 may be continually updated during the arrhythmia event to maintain an accurate account of the severity of the arrhythmia. Thus, the arrhythmia severity index 40 can provide an ongoing assessment of the arrhythmia severity throughout occurrence of an arrhythmia event or a patient. This may provide additional information about the progression of an arrhythmia event.

The arrythmia severity index 40 may be used to trigger an alert, escalate an alert, or de-escalate an alert. A large shortage of blood flow being caused by the arrythmia (large hemodynamic impact) may be indicated by the arrythmia severity index 40 having a large value. A small shortage in blood flow caused by the arrythmia (small hemodynamic impact) may be indicated by the arrythmia severity index 40 having a small value.

For example, a value of the arrhythmia severity index 40 may surpasses a predetermined threshold value as the arrhythmia severity index 40 is repeatedly updated. In response to the arrhythmia severity index 40 surpassing the threshold value, an alarm indicating an arrhythmia may be triggered since the arrhythmia severity index 40 indicates that the hemodynamic impact of the arrythmia is high. By ensuring that the arrhythmia detected in the ECG data is of a severity level that warrants an alarm before triggering an alarm, alarm fatigue and uncritical true alarms can be reduced. That is, noncritical alarms from arrhythmias that do not require clinician attention can be reduced. In some cases, a value of the arrhythmia severity index 40 surpassing a predefined threshold value can escalate or upgrade and alarm. For example, an alarm can be upgraded from minor to critical when the arrhythmia severity index 40 indicates that an arrhythmia has a severe hemodynamic impact. In a case where the arrhythmia severity index 40 drops below a predefined threshold value or fails to reach the threshold, indicating the hemodynamic impact is low, an alarm may be de-escalated or not triggered to prevent unnecessary usage of resources.

Once generated, the arrhythmia severity index 40 may be provided on a user interface display 18 to inform the clinician of the severity of the arrhythmia. In various embodiments, the arrhythmia severity index 40 may be depicted as timeseries data to inform the clinician of the hemodynamic impact of the arrhythmia over time. The graph of the arrhythmia index 40 may be displayed along with a graph of corresponding ECG data and pulse waveform data (e.g. PPG data). FIGS. 8A, 8B, 9, 10A, and 10B provide an exemplary array of graphs that may be displayed to the clinician. According to some embodiments, the graphs may be presented in response to a clinician selecting on an icon corresponding to an alarm. For example, an icon indicating the alarm may be displayed on a screen for monitoring one or more patients. By selecting the icon, the clinician may be presented with the data corresponding to the alarm, which, in this case may be the ECG data, blood flow data, and the arrhythmia severity index 40.

With reference also to FIG. 2, the patient monitor 10 may include a computing system 200 executing software 202 that performs the functions described herein, including the arrhythmia detection module 12 and the arrhythmia analysis module 14. The software receives the cardiac potentials 32, such as from the ECG monitor 3, which are processed by the arrhythmia detection module 12 to generate the arrhythmia indicator 33. The pulse waveform data 34 is also received from the arterial blood flow monitor 5. As described herein, the arrhythmia analysis module 14 may analyze the pulse waveform data 34 based on the cardiac pulse segments determined based on the cardiac potentials 32 and reference pulse waves obtained during normal heart beats. The pulse segments may be classified into a missed pulse, an altered pulse, or a normal pulse. A segment value for each pulse may then be determined based on the classification as well as the pulse morphology. The arrhythmia analysis module 14 may then generate the arrhythmia severity index 40 based on recent segment values. In certain embodiments, the arrhythmia analysis module 14 may be further configured to compare a present value of the arrhythmia severity index 40 to one or more severity thresholds, and to generate one or more arrhythmia severity alarms 42 when the arrhythmia severity index 40 exceeds a predetermined severity threshold.

FIG. 2 is a system diagram of an exemplary computing system 200 that includes a processing system 206, storage system 204, software 202, communication interface 208 and a user interface 210. The processing system 206 loads and executes software 202 from the storage system 204, including the arrhythmia detection module 12 and the arrhythmia analysis module 14, which are applications within the software 202. Each of the modules 12, 14 includes computer-readable instructions that, when executed by the computing system 200 (including the processing system 206), direct the processing system 206 to operate as described in herein in further detail, including to execute the steps to detect and analyze the severity of an arrhythmia.

Although the computing system 200 as depicted in FIG. 2 includes one software 202 encapsulating one arrhythmia detection module 12 and one arrhythmia analysis module 14, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 17, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the database 20, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the database 20. Likewise, database 20 can be stored, distributed, and/or implemented across one or more storage media or group of storage medias. Similarly, the database 20 may encompass multiple different sub-databases at different storage locations and/or containing different information which may be stored in different formats. The database 20 is configured to store the cardiac potentials 32, arrhythmia indicators 33, pulse waveform data 34, the reference pulse waveforms 36, and the arrhythmia severity index 40. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as to facilitate receipt of cardiac potentials from the ECG monitor 3 and/or pulse waveform data from the arterial blood flow monitor 5, UI devices such as the display 18 and speakers 19 (and/or user input devices such as a touchscreen or keyboard), and/or to facilitate communication with a central network of the healthcare facility (such as communicating the output values for storage in the patient's medical record).

Figure 3:
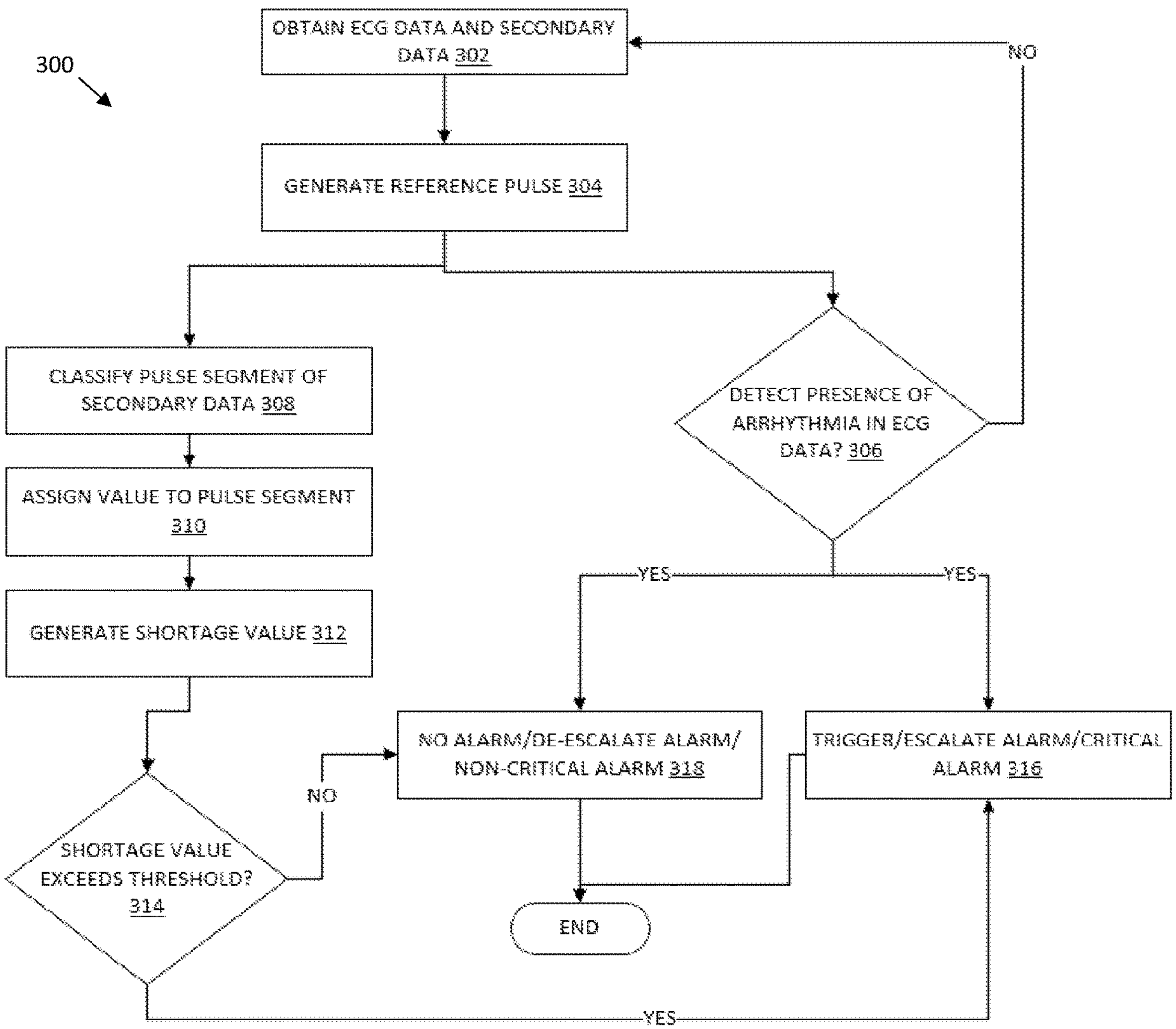
FIG. 3 is a flowchart of a method of monitoring cardiac arrhythmias, according to an example.

FIG. 3 is a flowchart of a method 300 of monitoring cardiac arrhythmias according to an example. The method of FIG. 3 may be performed on the patient monitoring system 1 of FIG. 1 and/or using the computing system 10 of FIG. 2. According to an aspect of the disclosure, the method 300 of FIG. 3 may be performed by multiple devices connected over a network. Method 300 may be used to monitor any type of arrythmia, such as atrial fibrillation and forms of tachycardia, such as ventricular tachycardia.

At operation 302, ECG data and secondary data may be obtained from a patient. Obtaining the ECG data may include measuring cardiac potentials from the patient via two or more electrodes 4 connected to the patient (e.g. 5, 8, or 12 lead ECG). The secondary data may be pulse waveform data corresponding to arterial blood flow of the patient. For example, the pulse waveform data may be obtained by measuring SpO2 of a patient using methods known in the art. According to other examples, the pulse waveform data may be obtained by a continuous blood pressure measurement which may produce a continuous stream of blood pressure data. According to some examples, the secondary data may be any data indicating blood flow of the patient.

At operation 304, a reference pulse may be generated. The reference pulse may be generated based on secondary data obtained during a time period where the ECG data indicates normal heart function. For example, a series of pulse waveforms may be obtained during the period of normal heart function. The series of pulse waveforms may then be analyzed or process to obtain the reference waveform. As an example, the reference waveform may be a median waveform out of the series pulse waveforms. According to another example, the reference waveform may be obtained by combining the series of pulse waveform to obtain an average waveform.

The reference waveform may be obtained when the patient is first connected to the monitor, and this waveform may be used through the entire monitoring process. Alternatively, each time an arrhythmia is detected, a new reference waveform may be generated based on secondary data obtained after the arrhythmia.

At operation 306, the ECG data may be analyzed to detect an arrhythmia. The arrhythmia detection based on ECG data may be performed using methods known in the art.

At operation 308, a pulse segment of the secondary data may be classified. A pulse segment of the secondary data may correspond to a beat of the patient's heart. The secondary data may be split into the pulse segments based on the ECG data. For example, heartbeats detected in the ECG data may be used to divide the secondary data into pulse segments. The disclosure is not limited to the above example, other methods known in the art may be used to detect heart beats for dividing the secondary data into pulse segments or for determining missed pulses.

According to an example, pulses may be detected in the secondary data over a period of time. This data may then be compared to heartbeat data, such as ECG data, taken from the same period of time to determine missed pulses. According to an example, the heart rate can be compared to the pulse rate to determine missed pulses.

Figure 4:
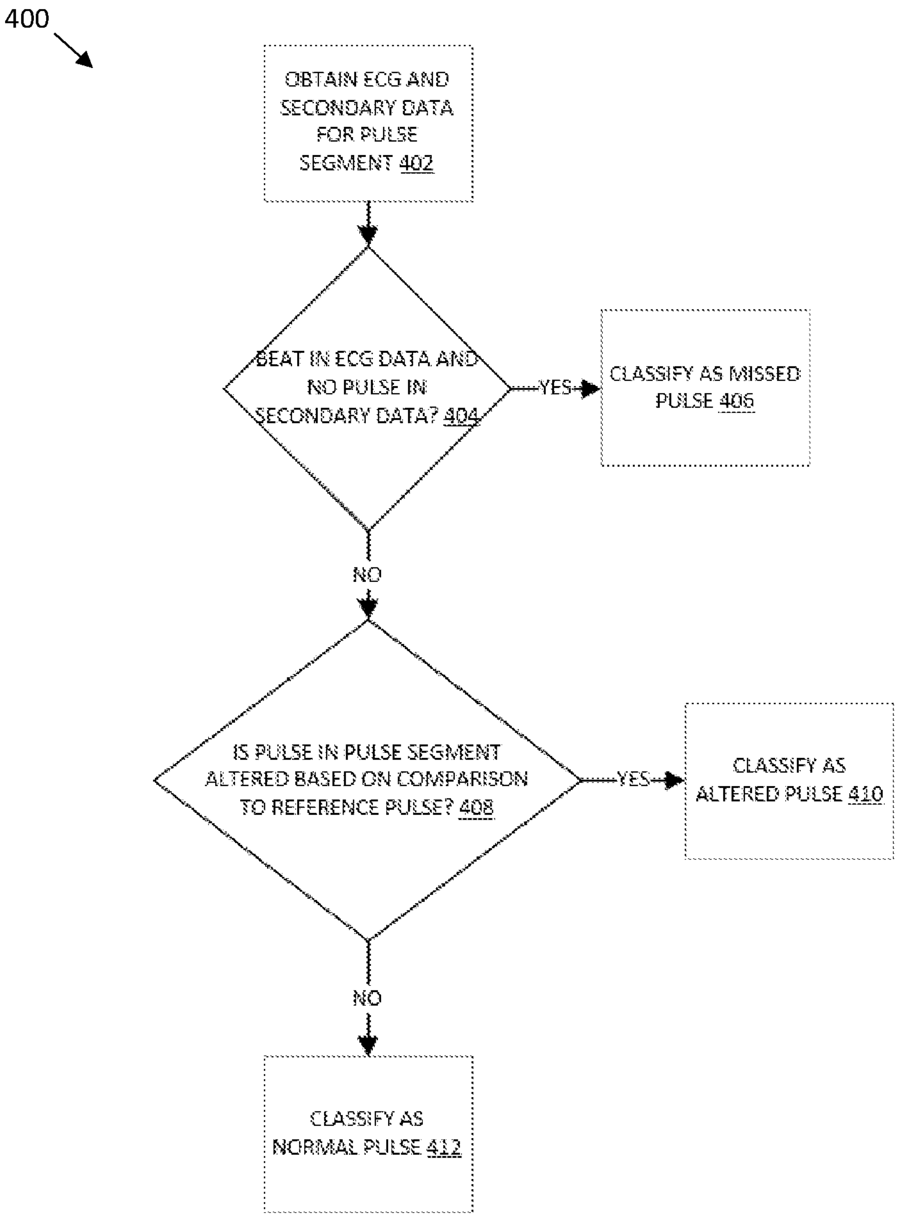
FIG. 4 is a diagram of a pulse segment classification process, according to an example.

A pulse segment may be classified into an altered (or small) pulse, a normal pulse, or a missed pulse. FIG. 4 is a diagram of the pulse segment classification process 400, according to an example.

At operation 404, ECG data and secondary data are analyzed to determine whether a pulse is missed. For example, if a pulse segment, which corresponds to a heartbeat in the ECG data, does not include a pulse, the pulse segment may be classified as a missed pulse, as shown in operation 406. A determination of a missed pulse may be based on analysis of the secondary data in the pulse segment. For example, detection of a positive slope over a period of time and then a negative slope over a period of time may indicate a pulse. Additionally or alternatively, an integral of the secondary data in the pulse segment may be used to determine whether the pulse segment includes a pulse. Additionally or alternatively, an range of change of the secondary data within the pulse segment may be used to determine whether the pulse segment includes a pulse. The disclosure is not limited the above examples, detection of a pulse may be performed using any method known in the art.

If a pulse is detected in the secondary data of the pulse segment, process 400 proceeds to operation 408 in which the pulse is compared to the reference pulse to determine if the pulse is altered or normal. The pulse height, pulse width, and/or morphology may be compared to the reference pulse or a metric obtained based on the reference pulse. For example, a value of an integral over the pulse may be compared to a value corresponding to an integral over the reference pulse. The value corresponding to the integral over the reference pulse may be less than the integral over the reference pulse, such as 20% less, since normal pulses may have a slight variation. If the integral over the pulse of the pulse segment is less than the value corresponding to the integral over the reference pulse, the pulse may be classified as an altered pulse in operation 410. Alternatively, if the integral over the pulse of the pulse segment is greater than the value corresponding to the integral over the reference pulse, the pulse may be classified as a normal pulse in operation 412.

According to another example, a pulse height may be obtained based on a size of the reference pulse. The pulse height of the pulse segment may be compared to the pulse height obtained based on a size of the reference pulse. If the height of the pulse in the pulse segment is less than the value corresponding to the pulse height obtained based on the reference pulse, the pulse may be classified as an altered pulse in operation 410. If the height of the pulse in the pulse segment is greater than the value corresponding to the pulse height obtained based on the reference pulse, the pulse may be classified as a normal pulse in operation 412. The above examples are not limiting, and the determination of altered versus normal pulse may be obtained based on a comparison between any metric that can be obtained from both the reference pulse and the pulse of the pulse segment.

At operation 310, a segment value may be assigned to the pulse segment based on the pulse morphology and/or the classification.

A value of a pulse segment may be obtained based on a slope of the pulse segment and a length of the pulse segment. The slope may be determined based on the pulse morphology and/or the classification. The length of the pulse segment may equate to the time period covered by the segment.

For a pulse segment that is classified as altered, the slope for the pulse segment may be determined using the following Equation 1.

$$\text{altered pulse slope} = \text{ratio of integrals} * \text{max\_slope} \quad \text{[Equation 1]}$$

Max_slope may be a predetermined constant, such as 1. The ratio of integrals may be defined by the following Equation 2.

$$\text{ratio of integrals} = \text{relative integral(reference pulse)} - \text{relative integral(current pulse)/relative integral (reference pulse)} \quad \text{[Equation 2]}$$

As shown in Equation 2, the ratio of integrals equals the difference of the relative integral of the reference pulse and the relative integral of the current pulse (e.g. pulse in pulse segment) divided by the relative integral of the reference pulse. A relative integral equals the integral over the pulse divided by the pulse length.

For a pulse segment that is classified as normal, the value of the pulse segment may be obtained by multiplying the max_slope constant by negative one. For a pulse segment that is classified as a missed pulse, the value of the pulse segment may be set as the max_slope constant. As such, the value for a normal pulse segment may by an additive inverse of the value for a missed pulse segment. According to other embodiments, the value of the normal pulse segment and the value of the missed pulse segment may be determined using different constants.

At operation 312, a shortage value may be generated. The shortage value may be determined based on a cumulative function in which the pulse segment value is added to a previous shortage value to obtain a new shortage value. A timeseries listing of the shortage values may make up the arrythmia severity index 40, which indicates the hemodynamic impact of an arrythmia. According to some examples, the shortage value may not fall below zero. That is, when the previous shortage value is zero and the segment value is negative, the shortage value may remain at zero.

At operation 314, the shortage value may be compared to one or more predefined thresholds. The threshold may be set based on the hemodynamic impact estimated by the shortage value. For example, a high impact threshold may be set at a level in which the severity of the arrythmia requires immediate attention from a clinician. A mid-impact threshold may be set at a level in which the severity of the arrythmia requires attention from a clinician, but not immediately. According to an aspect of the disclosure, the threshold may be determined by a clinician based on needs of the present scenario. For example, the threshold can be lowered in an instance where a higher sensitivity is desired, and the threshold may be raised in a scenario when a lower sensitivity is desired.

If the shortage value exceeds the threshold and an arrythmia is detected in the ECG data, an alarm may be triggered or escalated in operation 316. For example, since an arrythmia may not be severe enough to require immediate medical attention, an alarm may not be triggered solely based on an arrythmia being detected in the ECG data. Rather, to ensure that the hemodynamic impact of the arrythmia is sufficient to require triggering or escalation of an alarm, the alarm is not triggered or escalated until the arrythmia is detected in the ECG data and the shortage value exceeds a threshold.

If the shortage value does not exceed the threshold and an arrythmia is detected in the ECG data, an alarm may be de-escalated in operation 318. As discussed above, the attention of a clinician may not be necessary when the hemodynamic impact of an arrythmia is low. As such, if the shortage value does not exceed the threshold set for severe hemodynamic impact, the alarm will be de-escalated or not triggered since attention of a clinician is not necessary. According to an example, a non-critical or normal alarm may be triggered in operation 318 and a critical alarm may be triggered in operation 316.

In a case of a false ECG alarm, no alarm may be triggered in operation 318. For example, in a scenario in which the ECG signal includes a large amount of noise, an arrythmia may be falsely detected in the ECG data in operation 306. As such, a false positive alarm can be prevented by considering the shortage value before triggering an alarm.

According to an example, the shortage value may be compared to multiple thresholds that correspond to different tasks. For example, a lower threshold may trigger a non-critical alarm while a higher threshold may escalate the alarm to a critical alarm.

Figure 6:
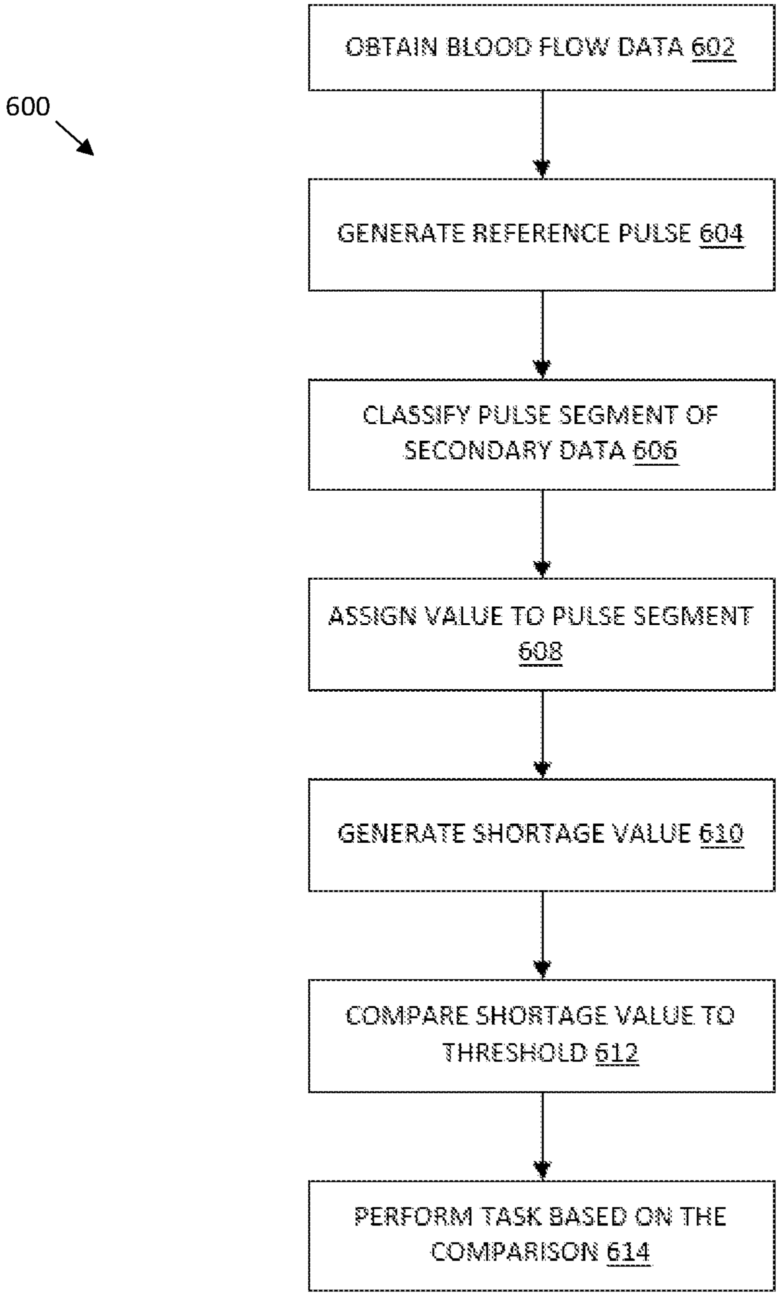
FIG. 6 is a flowchart of a method of monitoring cardiac arrhythmias, according to another example.

During method 300, as the ECG and secondary data are obtained, the secondary data may be continuously divided into pulse segments. Each pulse segment may then be assigned a value and applied to the cumulative arrythmia severity index 40 in real time (or near real time due to processing and data acquisition times). An example of the cumulative function is shown in FIG. 6.

In view of the above, in method 300, when an arrythmia is detected, a hemodynamic impact of the arrythmia is estimated based on the secondary data (e.g. SpO2 data, blood pressure data). By assessing the hemodynamic impact of the arrythmia, the severity of the arrythmia can be more accurately assessed by a monitoring device without the assistance of a caregiver. As such, by prioritizing arrythmias with a high hemodynamic impact and giving a lower priority to arrythmias with a low hemodynamic impact, a caregiver can more efficiently manage their time while also providing a higher standard of care.

Figure 5:
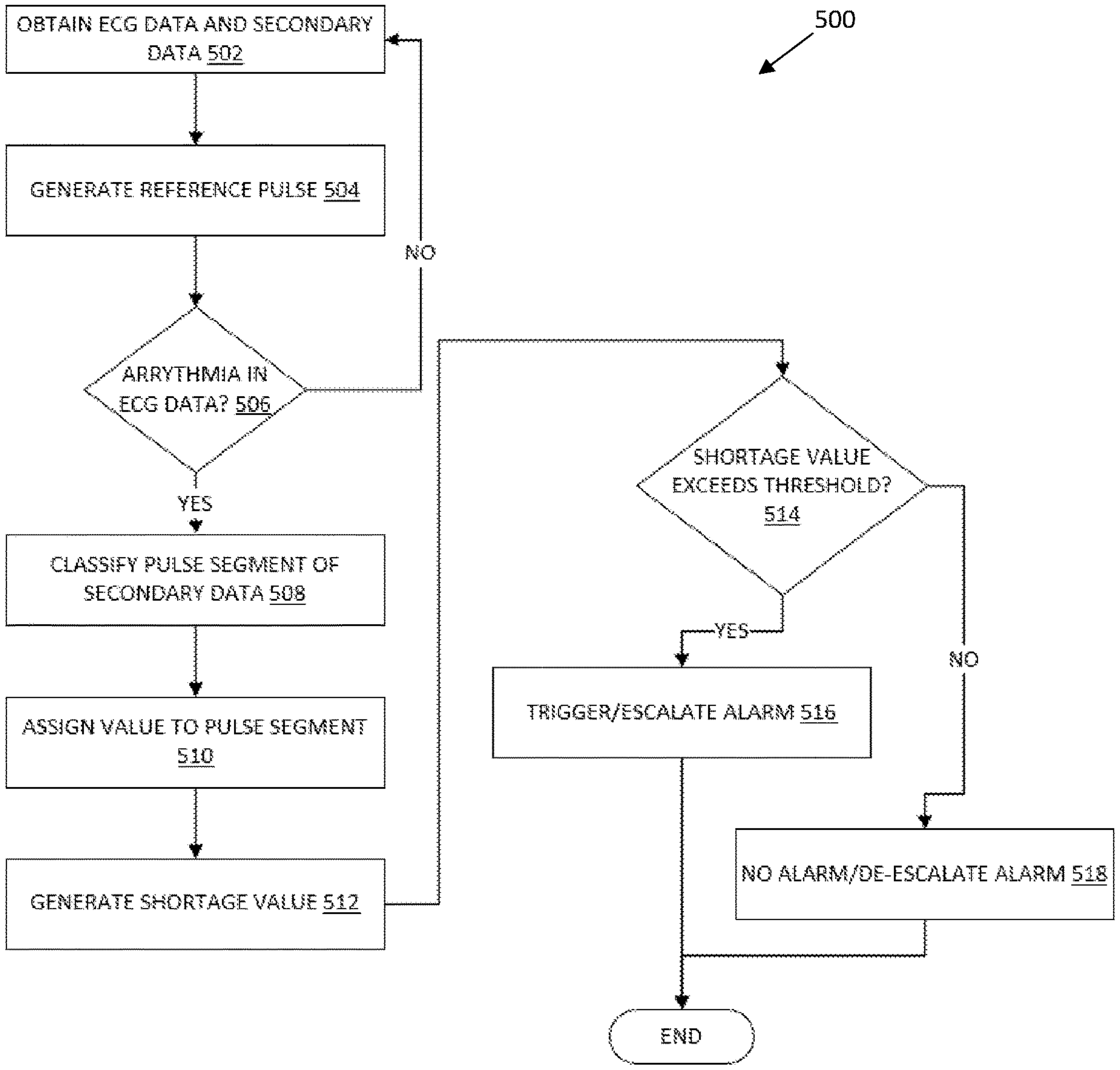
FIG. 5 is a flowchart of a method of monitoring cardiac arrhythmias, according to another example.

FIG. 5 is a flowchart of a method 500 of monitoring cardiac arrhythmias according to another example. The method of FIG. 5 may be performed on the patient monitoring system 1 of FIG. 1 and/or using the computing system 10 of FIG. 2. According to an aspect of the disclosure, the method 500 of FIG. 5 may be performed by multiple devices connected over a network. Method 500 may be used to monitor any type of arrythmia, such as atrial fibrillation and forms of tachycardia, such as ventricular tachycardia. Details of operations of method 500 that are similar to operations of method 300 may be omitted to avoid redundancies.

At operation 502, ECG data and secondary data may be obtained from a patient. This operation may be performed in a similar manner as operation 302.

At operation 504, a reference pulse may be generated. This operation may be performed in a similar manner as operation 304.

At operation 506, an arrythmia may be detected in the ECG data. This operation may be performed in a similar manner as operation 306.

Method 500 differs from method 300 in that method 500 performs the shortage value generation and comparison steps 508-518 based on an arrythmia being detected in the ECG data. As such, at operation 506, if an arrhythmia is not detected in the ECG data, the method 500 reverts back to operation 502. For example, if no arrhythmia is detected in the ECG data, data may be continuously collected without determining a severity of the arrhythmia. At operation 506, if an arrhythmia is detected in the ECG data, the method 500 proceeds to operation 508. For example, if an arrhythmia is detected, the severity of the arrhythmia may be estimated though operations 508-512 which estimate the hemodynamic impact of the arrythmia.

At operation 508, the pulse segment is classified based on the secondary data. This operation may be performed in a similar manner as operation 308.

At operation 510, a segment value may be assigned to the pulse segment based on the pulse morphology and/or the classification. This operation may be performed in a similar manner as operation 310.

At operation 512, a shortage value may be generated based on a previous shortage value and the segment value. This operation may be performed in a similar manner as operation 312.

At operation 514, the shortage value is compared to a threshold. Operation 514 may be performed in a similar manner as operation 314. If the shortage value exceeds the threshold, an alarm may be triggered or escalated in operation 516. If the shortage value does not exceed the threshold, an alarm may be de-escalated or no alarm may be triggered in operation 518. Operations 516 and 518 may be performed in a similar manner to operations 318 and 318, respectively.

Since method 500 generates the shortage index when an arrythmia is detected in the ECG data, method 500 may use less processing power and other resources.

FIG. 6 is a flowchart of a method 600 of monitoring cardiac arrhythmias according to another example. The method of FIG. 6 may be performed on the patient monitoring system 1 of FIG. 1 and/or using the computing system 10 of FIG. 2. According to an aspect of the disclosure, the method 600 of FIG. 6 may be performed by multiple devices connected over a network. Method 600 may be used to monitor any type of arrythmia, such as atrial fibrillation and forms of tachycardia, such as ventricular tachycardia. Details of operations of method 600 that are similar to operations of methods 300 and 500 may be omitted to avoid redundancies.

At operation 602, blood flow data may be obtained from a patient. The blood flow data may include pulse waveform data. The blood flow data may be obtained using methods known in the art such by measuring blood oxygen saturation or a continuous blood pressure measurement.

At operation 604, a reference pulse may be generated. This operation may be performed in a similar manner as operation 304.

At operation 606, a pulse segment a classified based on the secondary data. This operation may be performed in a similar manner as operation 308.

At operation 608, a segment value may be assigned to the pulse segment based on the pulse morphology and/or the classification. This operation may be performed in a similar manner as operation 310.

At operation 610, a shortage value may be generated based on a previous shortage value and the segment value. This operation may be performed in a similar manner as operation 312.

At operation 612, the shortage value may be compared to a threshold. Operation 612 may be performed in a similar manner as operation 314. If the shortage value exceeds the threshold, a task may be performed. For example, when the threshold is exceeded an alarm me be triggered or a message may be sent. According to an example, the shortage value may be compared to multiple thresholds that correspond to different tasks. A lower threshold may trigger a non-critical alarm while a higher threshold may escalate the alarm to a critical alarm.

Figure 7:
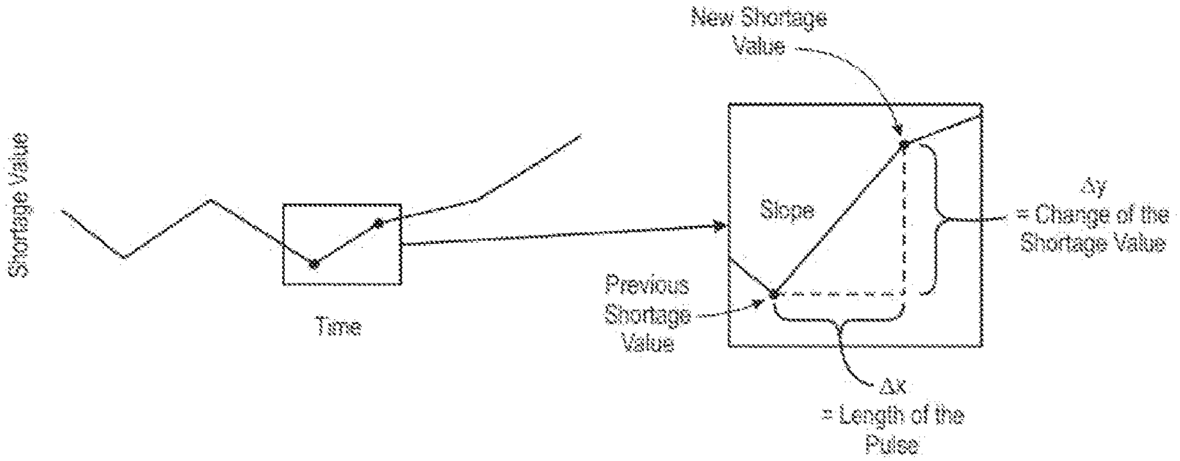
FIG. 7 shows an example of how the arrythmia severity index 40 is cumulatively calculated.

FIG. 7 shows an example of how the arrythmia severity index 40 is cumulatively calculated. The left-hand diagram in FIG. 7 shows an example of an arrythmia severity index 40 which includes multiple connected shortage values. The right-hand side of FIG. 6 shows how the values are calculated and combined to provide the cumulative arrythmia severity index 40.

As discussed above, in operation 310, a slope is calculated for a current pulse segment. A segment value ($\Delta y$) is then determined by multiplying the slope by the length of the pulse segment ($\Delta x$). A new shortage value is then determined by adding the segment value to the previous shortage value. This process is continuously repeated during the monitoring process to generate the arrythmia severity index 40.

Figure 8A:
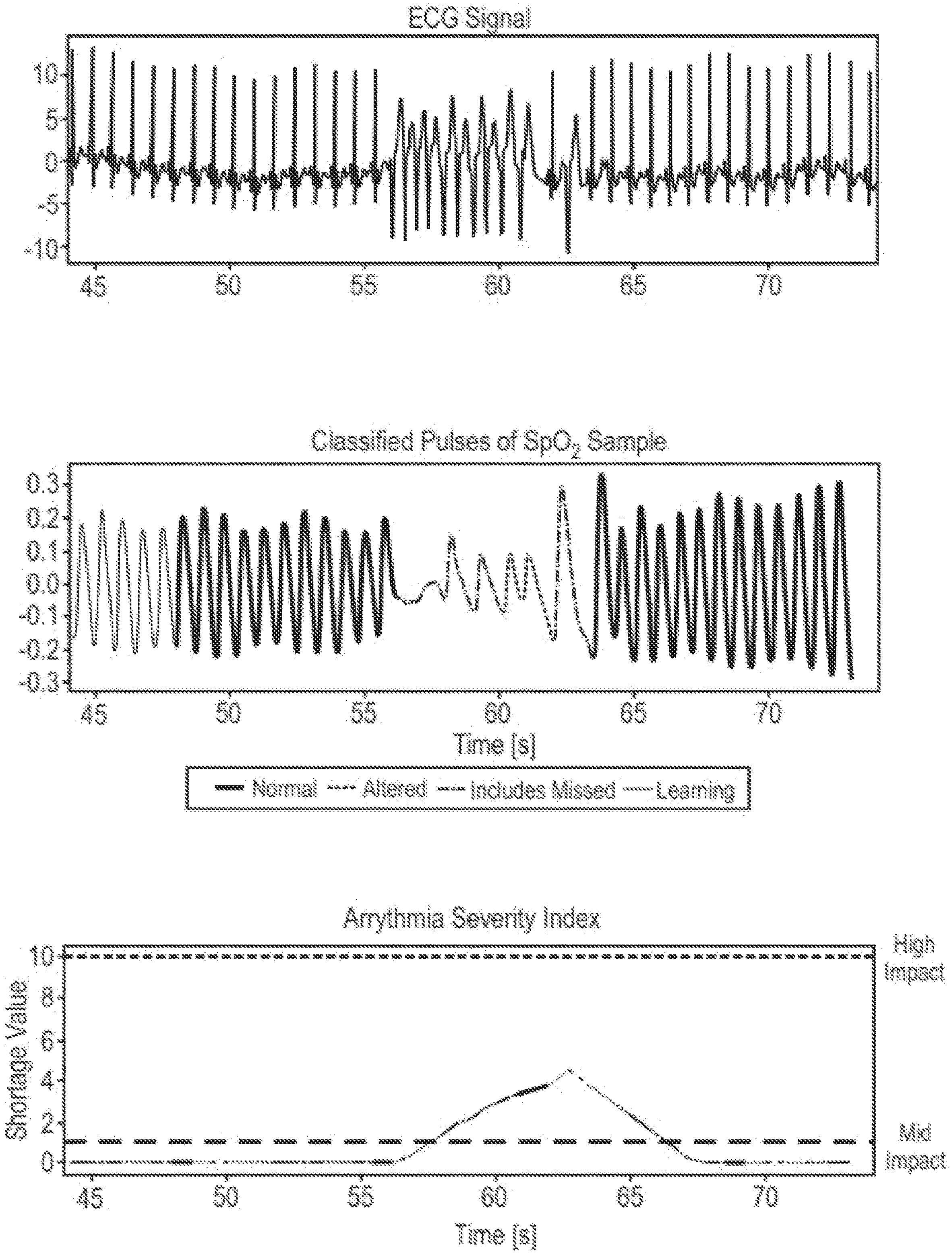
FIG. 8A shows graphs of an ECG signal, SpO2 data, and an arrythmia severity index for an example in which the arrythmia severity index indicates that the arrythmia is severe enough to trigger or escalate an alarm.
Figure 8B:
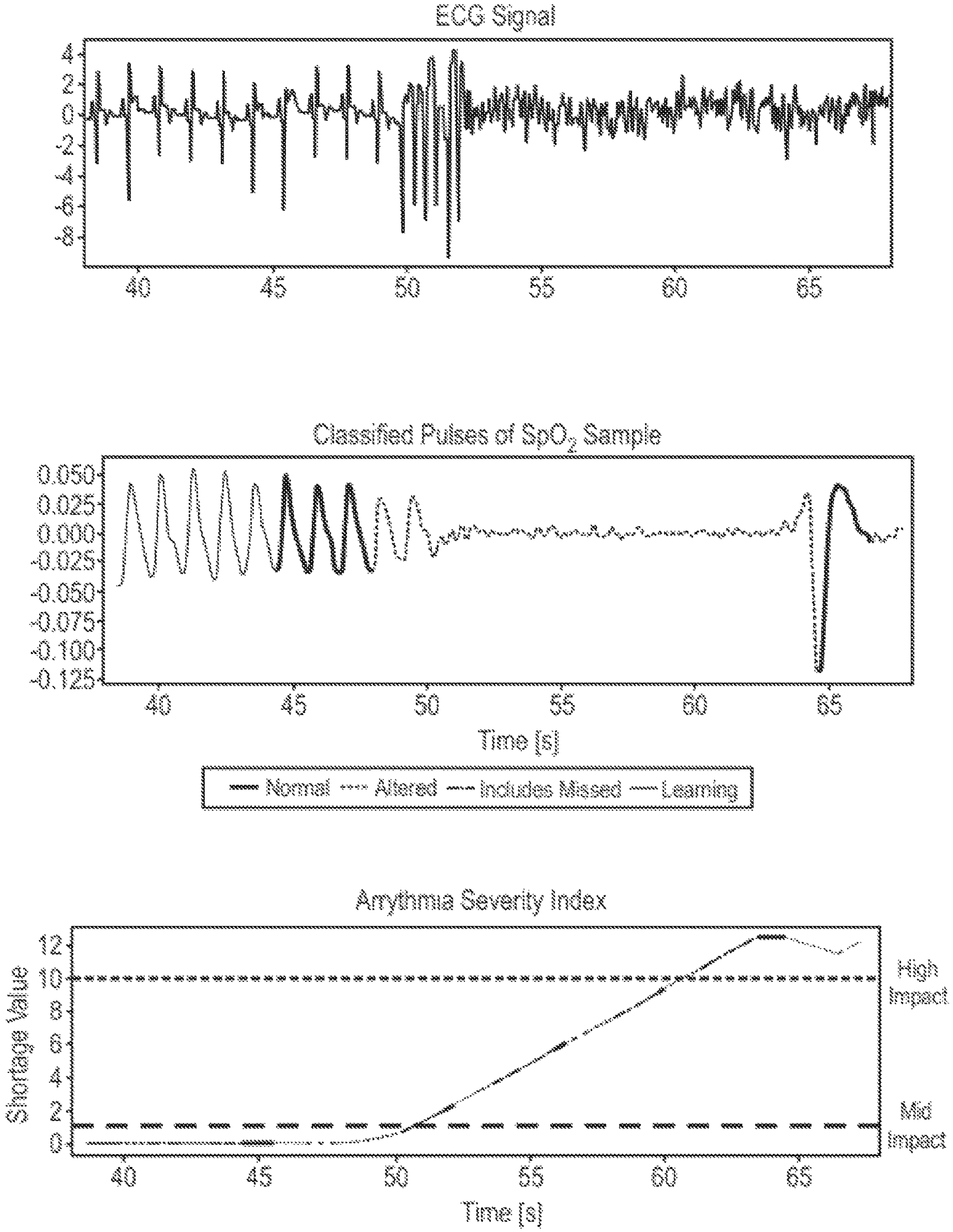
FIG. 8B shows graphs of an ECG signal, SpO2 data, and an arrythmia severity index for another example in which the arrythmia severity index indicates that the arrythmia is severe enough to trigger or escalate an alarm.
Figure 9:
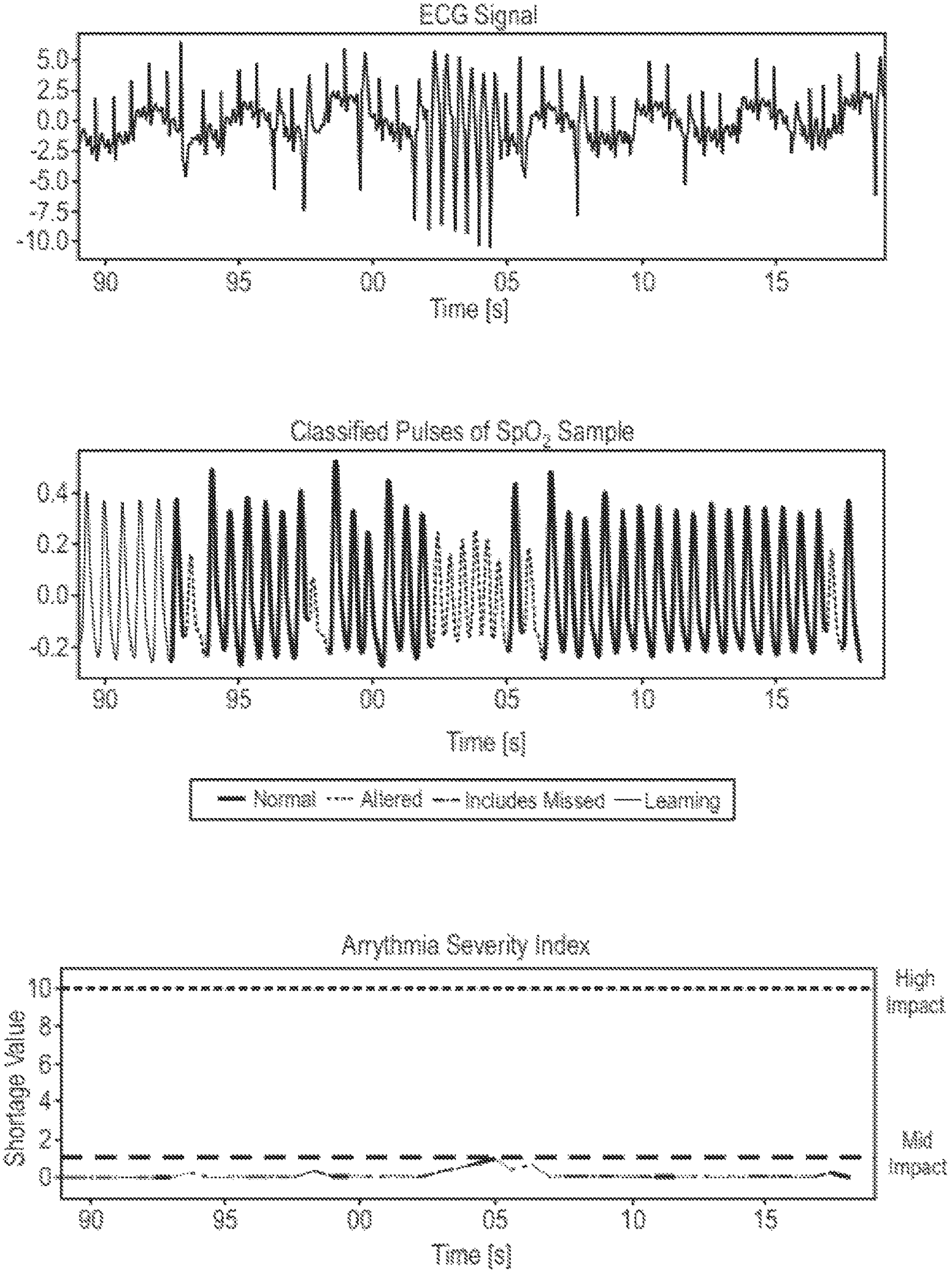
FIG. 9 shows graphs of an ECG signal, SpO2 data, and an arrythmia severity index for an example in which the arrythmia severity index indicates that the arrythmia is not severe enough to trigger or escalate and alarm.
Figure 10A:
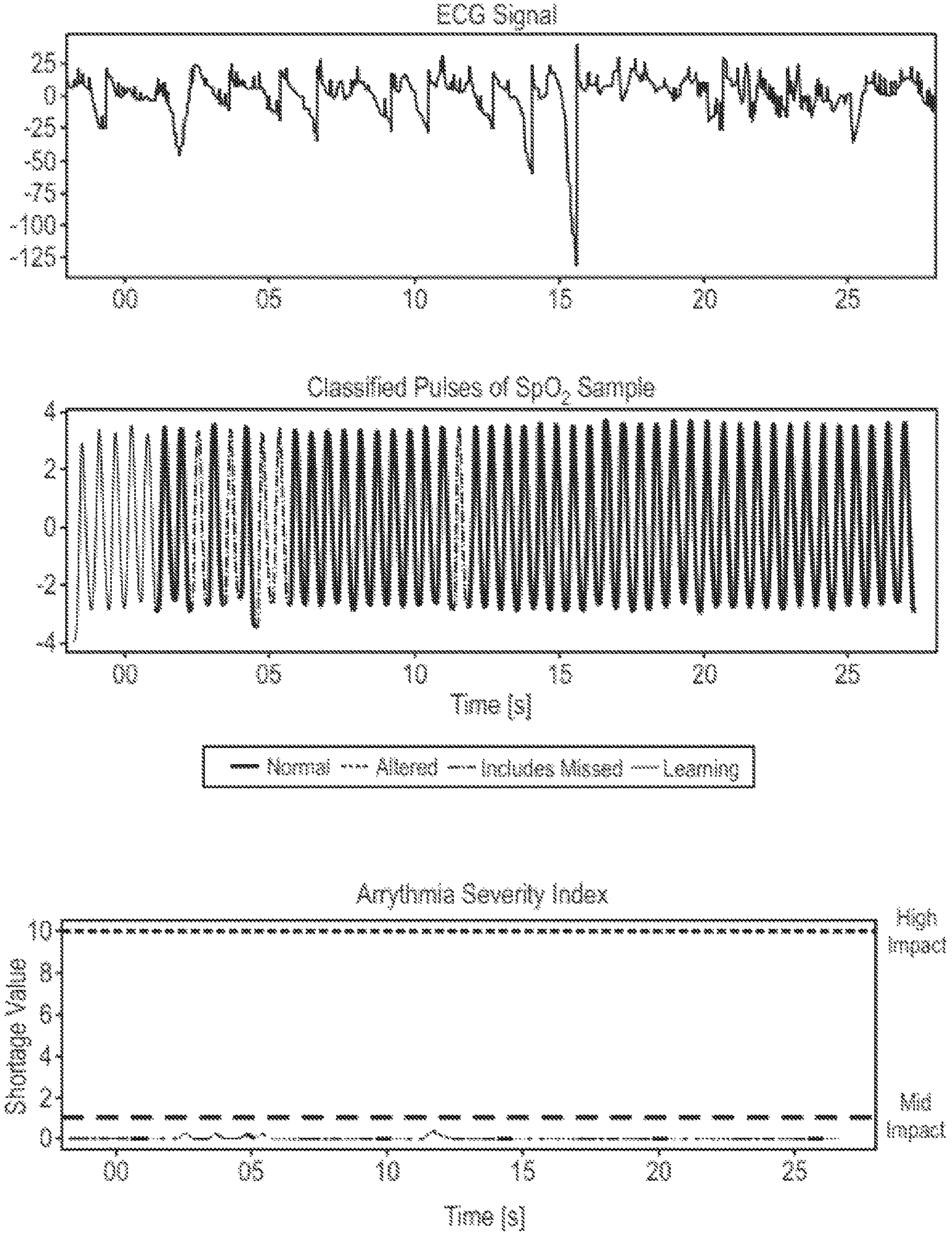
FIG. 10A shows graphs of an ECG signal, SpO2 data, and an arrythmia severity index for an example in which the arrythmia severity index indicates that the arrythmia detected in the ECG data may be a false detection.
Figure 10B:
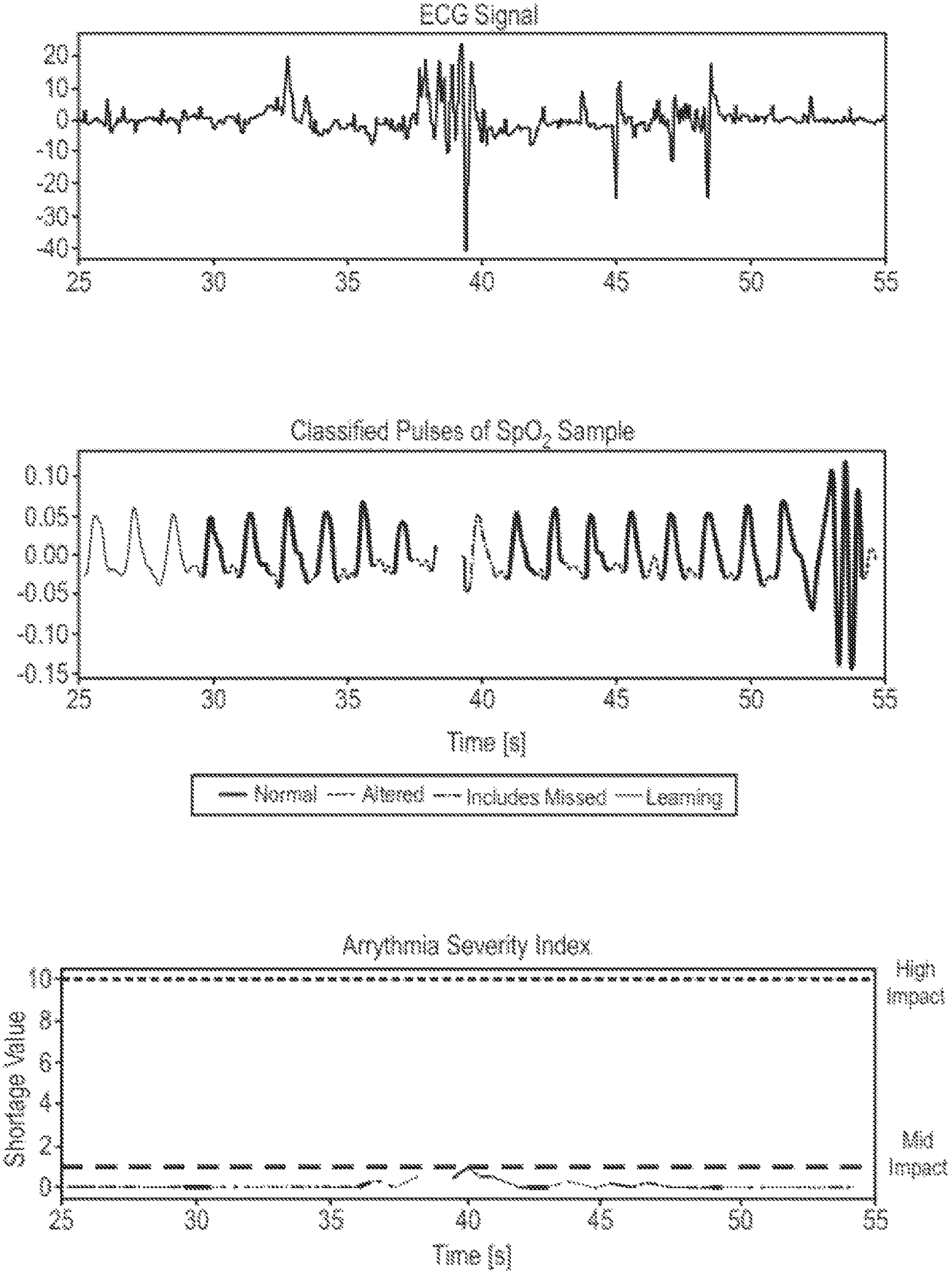
FIG. 10B shows graphs of an ECG signal, SpO2 data, and an arrythmia severity index for another example in which the arrythmia severity index indicates that the arrythmia detected in the ECG data may be a false detection.

FIGS. 8A, 8B, 9, 10A, and 10B show examples of arrythmia scenarios in ECG signals, SpO2 data, and arrythmia severity indexes 40. FIGS. 8A and 8B show instances in which the hemodynamic impact, as estimated by the shortage value, indicates that the arrythmia is sever/critical enough to trigger or escalate an alarm. FIG. 9 show an instance in which the hemodynamic impact, as estimated by the shortage value, indicates that the arrythmia is not sever/critical so no alarm should be triggered. FIGS. 10A and 10B show instances in which the arrythmia severity index indicates that the arrythmia detected in the ECG data may be a false detection.

As shown in FIG. 8A, an initial stage may be a learning phase where the monitor may process the incoming data to set parameters for performing the arrythmia monitoring method. For example, during the learning phase, a reference pulse may be obtained and parameters for determining pulse segments may be set. During the learning phase, the secondary data may be analyzed in a similar manner as the monitoring phase. This analysis may then be used for classifying the pulses in the monitoring phase. The learning phase differs from the monitoring phase in that there is no comparison to the reference parameters, rather the reference parameters are defined. During the learning stage, the shortage values and associated slopes may be set to zero.

As shown at approximately second 48, the learning process ends and the monitoring process begins. Since, at this time, the SpO2 data indicates normal pulses, the arrythmia severity index remains at 0. That is, since a normal pulse corresponds to a negative value, and since the shortage value cannot fall below zero, the arrythmia severity index 40 remains constant at zero indicating no blood flow shortage.

At approximately second 56, an arrythmia begins, as shown in both the ECG signal and the SpO2 data. As shown by the SpO2 data, the pulses are altered (e.g. much smaller than normal). As such, for each of these altered pulses, the segment value is determined based on Equation 1. As shown by Equation 1, if an integral over the pulse is small relative to an integral over the reference pulse, the segment value will be positive. Accordingly, as shown in FIG. 8A, for each of the altered pulses, the arrythmia severity index increases relative to the size of the pulses.

From approximately seconds 57-60, the SpO2 data indicates missed pulses. That is, the pulses shown in the SpO2 data last longer than a single heartbeat, thus indicating pulses were missed. As discussed above, the segment value for a missed pulse is the positive. Accordingly, as shown in FIG. 8A, the arrythmia severity index rises from seconds 57-60 due to the missed pulses.

As shown in FIG. 8A, the SpO2 data indicates altered pulses from approximately 60 to 62 seconds and missed pulses from approximately 62-63 second. These are reflected as increases in the arrythmia severity index.

At approximately second 64, the SpO2 data reverts back to normal pulses. As shown in the arrythmia severity index graph, the arrythmia severity index 40 descends back to zero since a segment value for normal pulses is a negative.

As shown in FIG. 8A, a high hemodynamic threshold may be set at the value of 10 on the arrythmia severity index and a mid-hemodynamic impact threshold may be set at 1 on the arrythmia severity index. According to an example, the mid-hemodynamic impact threshold may trigger a non-critical alarm and the high hemodynamic impact threshold may escalate the alarm to a critical alarm. In the example of FIG. 8A, the non-critical alarm may be triggered from approximately seconds 57-67 while the hemodynamic impact of the arrythmia is estimated to be a concern based on the values of the arrythmia severity index over that time. In this example, the hemodynamic impact was not estimated to be high enough to trigger the critical alarm. According to another example, based on the data in FIG. 8A, a non-critical alarm may be triggered based on the ECG data indicating an arrythmia and a critical alarm may be triggered based on the arrythmia severity index exceeding the lower threshold.

As shown in the example of FIG. 8B, approximately 15 seconds of missed and altered pulse caused the arrythmia severity index to exceed the high hemodynamic impact. In this example, this extended duration of missed and altered pulses indicates a severe shortage in blood flow and a very severe arrythmia. As such, the alarm was triggered and escalated to critical as both thresholds were exceeded by the arrythmia severity index.

As shown in the example of FIG. 9, the altered pulses caused by the arrythmia only lasts for a brief period of time, and the altered pulses are not much smaller than the normal pulses. As shown by the arrythmia severity index graph, these altered pulses caused by the arrythmia have a low hemodynamic impact. Since the hemodynamic impact of the altered pulses is not high enough to reach the mid-hemodynamic impact threshold, an alarm may not be triggered or an already triggered alarm may not be escalated.

In FIG. 10A, the ECG signal includes a large amount of noise. Accordingly, even though the patient is not experiencing an arrythmia, an arrythmia is detected in the ECG data. In this case, since the patient is not experiencing an arrythmia, the arrythmia severity index is low. Accordingly, a false alarm can be avoided since the arrythmia severity index does not extend above the lower threshold to trigger the alarm. However, in order to claim a false alarm, additional false detection analysis may need to be performed.

FIG. 10B also shows an example in which the ECG data is inaccurate. Similar to the example of FIG. 10A, a false alarm may be avoided since the arrythmia severity indicator does not exceed the threshold.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

We claim:

1. A system for monitoring cardiac arrhythmias, the system comprising:

an ECG monitor configured to obtain ECG data, the ECG data being obtained by measuring cardiac potentials during cardiac cycles;

a blood flow monitor configured to obtain secondary data, the secondary data being obtained by measuring a physiological parameter indicative of blood flow;

a memory storing instructions; and one or more processors configured to execute the instructions to perform the following operations in real time or near real time:

obtain the ECG data and the secondary data;

synchronize the ECG data and the secondary data according to a time of recording;

detect heartbeats in the ECG data;

obtain a pulse segment from a portion of the synchronized secondary data corresponding to a first heart beat in the ECG data;

classify the pulse segment based on pulse morphology, the classification comprising one or more of detecting a slope, a length, and an integral of the pulse segment;

assign a segment value to the pulse segment based on the classification, the segment value being based on one or more of the slope, the length, and the integral of the pulse segment;

calculate a shortage value based on a cumulative function in which a previous shortage value is added to the segment value;

update the shortage value in response to detecting a second heartbeat in the ECG data; and generate an arrhythmia severity indicator based on the shortage value in which a severity of the indicator tracks a change in the shortage value as the shortage value is updated.

2. The system of claim 1, wherein the ECG monitor comprises one of a 5 lead, an 8 lead, and a 12 lead ECG monitoring system.

3. The system of claim 1, wherein the blood flow monitor comprises a blood pressure monitor configured to provide a continuous blood pressure measurement.

4. The system of claim 1, wherein blood flow monitor comprises a pulse oximeter configured to provide a photoplethysmography measurement.

5. The system of claim 1, wherein the one or more processors are further configured to execute the instructions to trigger or escalate an alarm indicating a cardiac arrhythmia in response to the shortage value exceeding a predefined threshold.

6. The system of claim 1, wherein the pulse segment classifications comprise a normal pulse, an altered pulse, and a missed pulse.

7. The system of claim 6, wherein the one or more processors are further configured to execute the instructions to assign a value to the pulse segment by:

assigning a first segment value based on the pulse segment being classified as having the altered pulse;

assigning a second segment value based on the pulse segment being classified as having the missed pulse; and assigning a third segment value based on the pulse segment being classified as having the normal pulse, wherein the first segment value, the second segment value, and the third segment value each have different values.

8. The system of claim 7, wherein the one or more processors are further configured to execute the instructions to calculate the first segment value by:

calculating an integral of the secondary data over the pulse segment;

dividing the integral by a length of the pulse segment to obtain a relative integral of the pulse segment;

subtracting the relative integral of the pulse segment from a relative integral of a reference pulse to obtain a pulse difference; and dividing the pulse difference by the relative integral of the reference pulse.

9. The system of claim 7, wherein the third segment value is a preset value and the second segment value is an additive inverse of the third segment value.

10. The system of claim 6, wherein the one or more processors are further configured to execute the instructions to:

detect a pulse in the first pulse segment; and based on detecting the heart beat in the ECG data and not detecting a pulse in first pulse segment, determine that the pulse segment is a missed pulse.

11. The system of claim 6, wherein the one or more processors are further configured to execute the instructions to classify the normal pulse and the altered pulse by comparing the pulse segment to a reference pulse.

12. The system of claim 11, wherein the one or more processors are further configured to execute the instructions to obtained the reference pulse based on previously recorded secondary data during beats classified as normal based on the ECG data.

13. The system of claim 12, wherein the one or more processors are further configured to execute the instructions to obtain the reference pulse based on one or more of a median pulse or a mean pulse of the previously recorded secondary data.

14. The system of claim 1, wherein the arrythmia severity indicator comprises a shortage index based on the shortage value and at least one previous shortage value.

15. The system of claim 1, wherein the one or more processors are further configured to execute the instructions to calculate the segment value by multiplying the slope of the pulse segment by the length of the pulse segment.

16. The system of claim 1, wherein the one or more processors are further configured to execute the instructions to set the pulse segment based on the segment of the ECG data corresponding to a heartbeat.

17. A system for monitoring cardiac arrhythmias, the system comprising:

an ECG monitor configured to obtain ECG data, the ECG data being obtained by measuring cardiac potentials during cardiac cycles;

a blood flow monitor configured to obtain secondary data, the secondary data being obtained by measuring a physiological parameter indicative of blood flow;

a memory storing instructions; and one or more processors configured to execute the instructions to perform the following operations in real time or near real time:

obtain the ECG data and the secondary data;

synchronize the ECG data and the secondary data according to a time of recording;

detect heartbeats in the ECG data;

obtain a pulse segment from a portion of the synchronized secondary data corresponding to a first heart beat in the ECG data;

classify the pulse segment of secondary data based on pulse morphology, the classification comprising one or more of detecting a slope and a length of the pulse segment;

assign a slope to the pulse segment based on the classification;

multiply the slope of the pulse segment by a length of the pulse segment to obtain a segment value;

calculate a shortage value based on a cumulative function in which a previous shortage value is added to the segment value;

update the shortage value in response to detecting a second heartbeat in the ECG data;

compare shortage value to a predefined threshold; and trigger an alarm based on the shortage value exceeding the predefined threshold.

18. The system of claim 17, wherein the pulse segment classifications comprise a normal pulse, an altered pulse, and a missed pulse, and wherein the one or more processors are further configured to execute the instructions to assign a value to the pulse segment by:

assigning a first segment value based on the pulse segment being classified as having an altered pulse;

assigning a second segment value based on the pulse segment being classified as having a missed pulse; and assigning a third segment value based on the pulse segment being classified as having a normal pulse, wherein the first segment value, the second segment value, and the third segment value each have different values.

19. The system of claim 18, wherein the third segment value is a preset value and the second segment value is an additive inverse of the third segment value, and wherein the one or more processors are further configured to execute the instructions to calculate the first segment value by:

calculating an integral of the secondary data over the pulse segment;

dividing the integral by a length of the pulse segment to obtain a relative integral of the pulse;

subtracting the relative integral of the pulse segment from a relative integral of the reference pulse to obtain a pulse difference; and dividing the pulse difference by the relative integral of the reference pulse.

20. A method for monitoring cardiac arrhythmias, the method comprising:

obtain ECG data generated by an ECG monitor and secondary data generated by a blood flow monitor;

synchronize the ECG data and the secondary data according to a time of recording;

detecting heartbeats in the ECG data;

obtaining, in real time or near real time, a pulse segment from a portion of the synchronized secondary data corresponding to a first heart beat in the ECG data;

classifying, in real time or near real time, the pulse segment based on pulse morphology, the secondary data indicating blood flow, the classification comprising one or more of detecting a slope, a length, and an integral of the pulse segment;

assigning, in real time or near real time, a segment value to the pulse segment based on the classification, the segment value being based on one or more of the slope, the length, and the integral of the pulse segment;

calculating, in real time or near real time, a shortage value based on a cumulative function in which a previous shortage value is added to the segment value;

updating, in real time or near real time, the shortage value in response to detecting a second heartbeat in the ECG data; and generating, in real time or near real time, an arrhythmia severity indicator based on the shortage value in which a severity of the indicator tracks a change in the shortage value as the shortage value is updated.

* * * * *